United States Patent [19]

Stephen et al.

[11] Patent Number: 4,593,057

[45] Date of Patent: Jun. 3, 1986

[54] HINDERED PHENOLIC COMPOUNDS DERIVED FROM HEXITANS AND STABILIZED COMPOSITIONS

[75] Inventors: John F. Stephen, West Chester, Pa.; Jerry H. Smith, Wilmington, Del.

[73] Assignee: ICI Americas Inc., Wilmington, Del.

[21] Appl. No.: 765,679

[22] Filed: Aug. 15, 1985

[51] Int. Cl.[4] ..................... C08K 5/15; C07D 307/24
[52] U.S. Cl. .................................. 524/111; 524/291; 549/476
[58] Field of Search ............... 524/111, 291, 107, 109, 524/110; 549/476, 478; 528/283; 560/92

[56] References Cited

U.S. PATENT DOCUMENTS

| | | | |
|---|---|---|---|
| 2,720,507 | 10/1955 | Caldwell | 528/283 |
| 3,285,855 | 11/1966 | Dexter et al. | 524/291 |
| 3,484,459 | 12/1969 | Hartmann | 549/478 |
| 3,962,313 | 6/1976 | Dexter et al. | 524/291 |
| 4,529,666 | 7/1985 | Salzburg et al. | 524/111 |

FOREIGN PATENT DOCUMENTS 4112746 7/1979 Japan.
1010257 11/1965 United Kingdom.

*Primary Examiner*—Veronica P. Hoke
*Attorney, Agent, or Firm*—Richard A. Rowe

[57] ABSTRACT

Novel phenolic compounds derived from hexitans are disclosed which are useful stabilizers of synthetic polymer resins. A process for manufacture of these stabilizers is also provided.

7 Claims, No Drawings

HINDERED PHENOLIC COMPOUNDS DERIVED FROM HEXITANS AND STABILIZED COMPOSITIONS

The present invention relates to novel hindered phenolic compounds derived from hexitans, to stabilized polymer resins containing these materials, and to methods for there preparation. It also relates to resins containing the novel stabilizers with costabilizers including thio-synergists and phosphites.

The compounds of this invention have the following general formula:

$$C_6H_8O_5R_4$$

where R is:

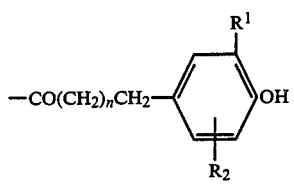

wherein $R^1$ and $R^2$ are independently H or alkyl groups of from 1 to 8 carbon atoms or cycloalkyl groups having from 5 to 12 carbon atoms; n has a value of 1 to 6; and $C_6H_8O_5$ is a hexitan moiety also referred to as a hexitol monoanhydride.

Examples of such hexitans include 1,4-anhydro-D-sorbitol(arlitan or 1,4-sorbitan); 1,5-anhydro-D-sorbitol(polygalitol); 3,6-anhydro-D-sorbitol(3,6-sorbitan); 1,4-(3,6)-anhydro-D-mannitol(mannitan); 1,5-anhydro-D-mannitol(styracitol); 3,6-anhydro-D-galactitol; 1,5-anhydro-D-galactitol; 1,5-anhydro-D-talitol; and 2,5-anhydro-L-iditol.

The preferred hexitan is derived by the anhydridization of sorbitol to form for example 1,4-sorbitan, 3,6-sorbitan and 2,5-anhydro-L-iditol.

Preferably at least one of $R^1$ and $R^2$ must be in the ortho position to the hydroxy group on the benzene ring. Most preferred is the compound having both $R^1$ and $R^2$ in the ortho position to the hydroxyl group.

The preferred compound has $R^1=R^2=$t-butyl, n=2, and $(C_6H_8O_5)=$1,4-sorbitan as follows:

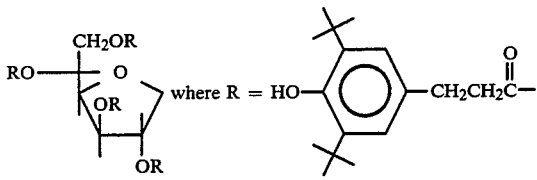

This invention relates to hindered phenolic esters derived from individual hexitans as well as mixtures containing esters of more than one hexitan. For example, a mixture derived from anhydrization of sorbitol could contain hindered phenolic esters of 1,4-sorbitan, 3,6-sorbitan, and 2,5-anhydro-L-iditol.

This invention also relates to a process for preparing the compounds described herein. Typical transesterification catalysts such as sodium methoxide, lithium hydride, potassium carbonate, and lithium amide can be used for preparing the compounds of this invention from the hexitan and a lower alkyl ester containing a hindered phenol group. However, these catalysts give only moderate yields (30–80%) and impart color to the product which is difficult to remove. It has been discovered that certain organotin compounds such as dialkyl tin dialkanoates are very effective catalysts giving higher yields (90–100%) of an almost colorless product needing little or no purification. The dialkylportion of the catalyst may be selected from compounds having 2–12 carbon atoms while the alkanoate moiety may be selected from acids having 2–20 carbon atoms. These catalysts may be selected from compounds such as dibutyl tin dilaurate, dibutyl tin diacetate, and dibutyl tin di(2-ethylhexanoate). The catalyst can be removed from the reaction product by extraction and filtration.

The hexitan starting materials can be prepared by procedures such as outlined in U.S. Pat. Nos. 3,480,651; 3,484,459; and Saltzburg et al., J. Am. Chem. Soc., 68, 919 (1946). Suitable lower alkyl esters of ROH containing the hindered phenolic group are prepared by known methods such as outlined in U.S. Pat. Nos. 3,330,859 and 3,364,250.

This invention also relates to stabilized compositions containing the compounds described herein.

The compounds of this invention are stabilizers of organic material normally subject to thermal and oxidative deterioration. Materials which are thus stabilized include synthetic organic polymeric substances such as vinyl resins formed from the polymerization of vinyl halides or from the copolymerization of vinyl halides with unsaturated polymerizable compounds, e.g., vinylesters, $\alpha,\beta$-unsaturated ketones, $\alpha,\beta$-unsaturated aldehydes, and unsaturated hydrocarbons such as butadienes and styrene; poly-$\alpha$-olefins such as polyethylene, polypropylene, polybutylene, and the like, including copolymers of poly-$\alpha$-olefins, polyurethanes and polyamides such as polyhexamethylene adipamide and polycaprolactam; polyesters such as polyethylene terephthalates; polycarbonates; polyacetals; polystyrene; polyethyleneoxide; polyisoprene; polybutadiene and copolymer such as those of high impact polystyrene containing copolymers of butadiene and styrene and those formed by the copolymerization of acrylonitrile, butadiene and/or styrene.

In general, one or more of the stabilizers of the present invention are employed in amounts ranging from about 0.005 to about 5% by weight of the composition to be stabilized. A particularly advantageous range of the present stabilizers is from about 0.05% to about 2%. The preferred range is particularly effective in polyolefins such as polypropylene.

These compounds may be incorporated in the polymer substance during the usual processing operations, for example, by milling, or extrusion. The stabilized polymer can be fabricated into films, filaments, hollow-spheres and the like. The heat stabilizing properties of these compounds advantageously stabilize the polymer against degradation during such processing at the high temperatures generally encountered.

The stabilizers employed in this invention can also be used in combination with other stabilizers or additives. Especially useful co-stabilizers are dilauryl-$\beta$-thiodipropionate and distearyl-$\beta$-thiodipropionate.

The stabilizers described in this invention can be used in combination with di- and tri-alkyl and alkyl phenyl phosphites such as tris-nonylphenyl phosphite, tris(2,4-di-tert-butylphenyl)phosphite, bis(2,4-di-t-butyl phenyl)pentaerythritol diphosphite, tetrakis(2,4-di-tertbutylphenyl)-4,4′-biphenylene diphosphonite, and distearyl pentaerythritol diphosphite.

Other antioxidants, antiozonants, thermal stabilizers, ultraviolet light absorbers, coloring materials, dyes, pigments, metal chelating agents, etc., may also be used in the compositions in combination with the stabilizers of the invention.

EXAMPLE 1

1,4-Sorbitan tetrakis[3,(3,5-di-tert-butyl-4-hydroxyphenyl)propionate]

Methyl 3(3,5-di-tert-butyl-4-hydroxyphenyl)propionate (42.05 g) was added to a flask equipped with a reflux condenser heated with hot water (65° C.). The material was heated to 130° C. under $N_2$ with magnetic stirring. Sodium methoxide (0.16 g) was added and a vacuum (10 mm) was applied. After 25 min., the vacuum was broken with $N_2$ and 1,4-sorbitan (4.92 g) was added. Vacuum was reapplied and temperature was slowly increased to 150° C. After 6 hr., the reaction was quenched with acetic acid, taken up in ether, and extracted with water. Excess starting ester was removed by vacuum distillation. The crude material was chromatographed (Silica Gel, 8:2 hexane:ethyl acetate) to give 13.0 g (36%) of the desired product, mp 80°–85° C.

Calculated for $C_{74}H_{108}O_{13}$: C, 73.72; H, 9.03. Found: C, 73.73; H, 9.10.

EXAMPLE 2

In order to demonstrate the improved process of the invention, the compound of Example 1 was prepared by the following method. Methyl 3(3,5-di-tert-butyl-4-hydroxyphenyl)propionate (56.06 g) and 1,4-sorbitan (5.56 g) were added to a flask equipped with a nitrogen inlet and a reflux condenser heated with hot water (65° C.). The mixture was heated to 185° C. and stirred magnetically. Dibutyltin dilaurate (0.3 ml) was added and a vacuum (10 mm) was applied. After 11 hr., HPLC analysis showed a 96% conversion to the tetra ester. The melt was taken up in heptane and treated with NaOH solution to remove the catalyst. Excess starting ester was removed by vacuum distillation. The resulting glassy material was crushed to give a 45.0 g (93%) of a white powder, mp 80°–85° C.

EXAMPLE 3

This example shows the usefulness of the invention for stabilization of polypropylene. The stabilizers were incorporated into Profax 6301 TM polypropylene resin by solvent blending (methylene chloride) followed by extrusion at 200° C. Twenty-five mil plaques were prepared by compression molding at 6,000 psi and 188° C. Samples were tested in a forced draft oven at 150° C. Failure was determined when the first signs of decomposition were observed. Tests were run in quadruplicate and an average value was determined. Results are shown in Table I.

TABLE I

| Stabilizer | Concentration (%) | Hours to Failure |
|---|---|---|
| none | — | 24 |
| Example 1 | 0.10 | 1068 |
| Example 1/DSTDP | 0.10/0.25 | 2340 |

EXAMPLE 4

This example shows the usefulness of the invention for stabilization of high impact polystyrene. The stabilizers were incorporated into high impact polystyrene by milling at 188° C. Twenty mil plaques were prepared by compression molding at 6,000 psi and 188° C. Samples were tested in a forced draft oven at 90° C. Failure was determined when cracking was observed after flexing the plaque over a one-inch mandrel. Tests were run in quadruplicate and an average value was determined. Results are shown in Table II.

TABLE II

| Stabilizer | Concentration (%) | Hours to Failure |
|---|---|---|
| none | — | 48 |
| Example 1 | 0.10 | 336 |
| Example 1/DLTDP | 0.05/0.15 | 240 |

EXAMPLE 5

This example shows the usefulness of the invention for stabilization of high density polyethylene. The stabilizers were incorporated into high density polyethylene (Allied Chemical EA 55-003) by solvent blending (methylene chloride) followed by extrusion at 230° C. Twenty-five mil plaques were prepared by compression molding at 6,000 psi and 188° C. Samples were tested in a forced draft oven at 120° C. Failure was determined when cracking was observed after flexing. Tests were run in quadruplicate and an average value was determined. Results are shown in Table III.

TABLE III

| Stabilizer | Concentration (%) | Hours to Failure |
|---|---|---|
| none | — | 48 |
| Example 1 | .05 | 3456 |
| Example 1/Weston 618 | .025/0.5 | 3144 |

What is claimed is:

1. A hindered phenolic compound derived from a hexitan and having the general formula:

where R has the following formula:

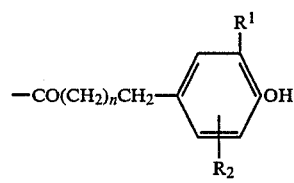

wherein $R^1$ and $R^2$ are independently hydrogen or alkyl groups of from 1 to 8 carbon atoms or cycloalkyl groups having from 5 to 12 carbon atoms; n has a value of 1 to 6, and $C_6H_8O_5$ is a hexitan structure.

2. A compound of claim 1 wherein $R^1$ and $R^2$ are tert-butyl groups and $R^2$ is ortho to the hydroxy.

3. A compound of claim 2 wherein n equals 2.

4. A compound of claim 3 wherein the hexitan is 1,4-sorbitan.

5. A composition comprising a polymer derived from ethylenically unsaturated monomer and 0.005–5% by weight of a compound of claim 1.

6. A composition of claim 5 comprising a resin selected from the group consisting of polyethylene, polypropylene, and polystyrene.

7. A composition of claim 6 further comprising a costabilizer compound selected from the group consisting of dilauryl-β-thiodipropionate, distearyl-β-thiodipropionate, distearyl pentaerythritol diphosphite, pentaerythritol tetrakis(3-(dodecylthio)propionate), tris(2,4-di-tert-butylphenyl)phosphite, bis(2,4-di-tert-butylphenyl)pentaerythritol diphosphite, and tetrakis(2,4-di-tert-butylphenyl)-4,4'-biphenylene diphosphonite.

* * * * *